(12) United States Patent
Teitell

(10) Patent No.: US 10,758,712 B2
(45) Date of Patent: Sep. 1, 2020

(54) MEDICAL DEVICE FOR TREATING ABSCESSES

(71) Applicant: SANTACRUZ TECHNOLOGY, LLC., Fairfield, CT (US)

(72) Inventor: Richard Teitell, Fairfield, CT (US)

(73) Assignee: SantaCruz Technology LLC, Fairfield, CT (US)

( * ) Notice: Subject to any disclaimer, the term of this patent is extended or adjusted under 35 U.S.C. 154(b) by 0 days.

(21) Appl. No.: 14/679,410

(22) Filed: Apr. 6, 2015

(65) Prior Publication Data

US 2016/0287448 A1 Oct. 6, 2016

(51) Int. Cl.
| | |
|---|---|
| *A61M 25/10* | (2013.01) |
| *A61M 27/00* | (2006.01) |
| *A61M 25/00* | (2006.01) |
| *A61F 13/45* | (2006.01) |
| *A61F 13/15* | (2006.01) |

(52) U.S. Cl.
CPC ............ *A61M 25/10* (2013.01); *A61M 27/00* (2013.01); *A61F 13/45* (2013.01); *A61F 2013/15008* (2013.01); *A61F 2013/4506* (2013.01); *A61M 2025/0056* (2013.01); *A61M 2025/105* (2013.01)

(58) Field of Classification Search
CPC ............ A61F 13/45; A61F 2013/15008; A61F 2013/4506; A61M 25/10; A61M 27/00; A61M 2025/0056; A61M 2025/105

USPC .......................................................... 604/14
See application file for complete search history.

(56) References Cited

U.S. PATENT DOCUMENTS

| | | | | |
|---|---|---|---|---|
| 5,498,251 | A * | 3/1996 | Dalton | A61M 25/0043 604/163 |
| 2003/0032963 | A1* | 2/2003 | Reiss | A61B 10/025 606/90 |
| 2005/0221072 | A1* | 10/2005 | Dubrow | A61F 2/30767 428/292.1 |
| 2008/0243103 | A1* | 10/2008 | Whetham | A61M 25/10 604/515 |
| 2009/0205643 | A1* | 8/2009 | Tanaka | A61K 9/007 128/200.24 |
| 2011/0040232 | A1* | 2/2011 | Magal | A61F 5/003 604/8 |
| 2012/0259401 | A1* | 10/2012 | Gerrans | A61F 2/958 623/1.11 |

* cited by examiner

*Primary Examiner* — Andrew J Mensh
(74) *Attorney, Agent, or Firm* — Ziegler IP Law Group, LLC

(57) ABSTRACT

A medical device is provided that is configured to treat and drain an abscess. The device comprises a catheter having an expandable distal end including a flexible absorbent material. The catheter includes an input port configured to receiving fluid from a syringe, whereby the fluid expands distal end when injected. Upon expansion of the distal end, the absorbent material expands into the abscess cavity.

19 Claims, 5 Drawing Sheets

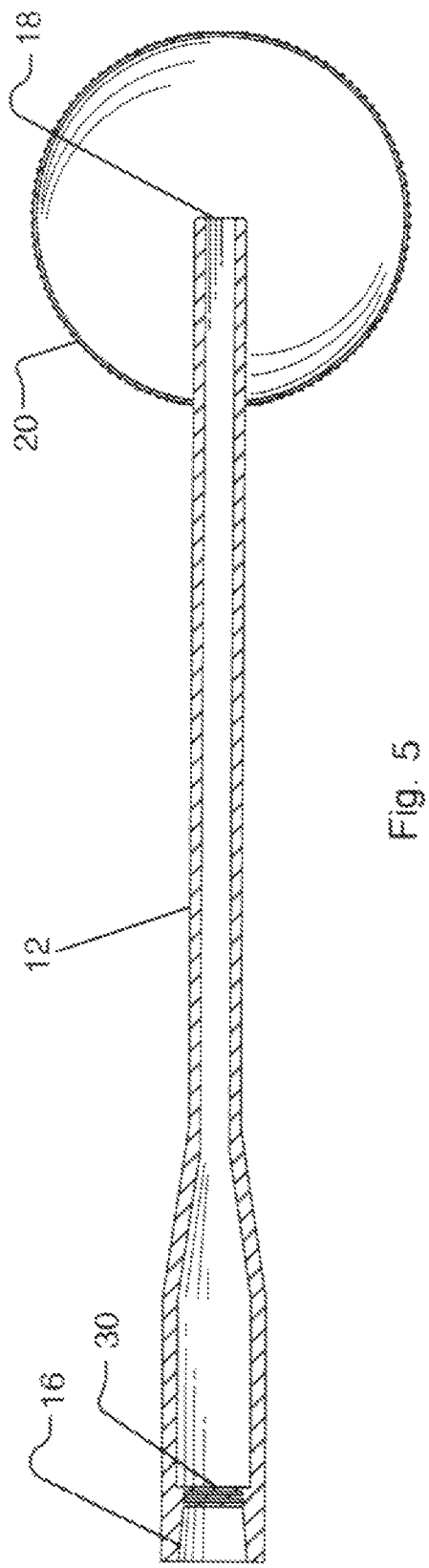

MEDICAL DEVICE FOR TREATING ABSCESSES

DESCRIPTION OF RELATED TECHNOLOGY

The conventional method of draining an abscess on the body typically involves packing the wound, which comprises inserting small amounts of gauze dressing into the wound until the cavity is filled. This is a time-consuming process and typically causes significant pain and discomfort to the patient. Also, the patient often must return to a physician for removal of the dressing and additional treatment.

SUMMARY

Described are embodiments of a medical device configured to treat and drain an abscess. The device comprises a catheter comprising an expandable distal end including a flexible absorbent material. The catheter further includes an input port configured to receive fluid from a syringe, whereby the fluid expands the distal end when injected. Upon expansion of the distal end, the absorbent material expands into the abscess cavity thereby packing the abscess. In any or all of the embodiments described, the device can include a drainage lumen configured to allow material from the abscess to drain through the output port.

In any or all of the embodiments described, the device can comprise a catheter that is at least partially or entirely flexible. In any or all embodiments described, the distal end of the catheter can comprise a balloon means and/or a flexible absorbing means. In any or all embodiments described, the catheter includes an input means for receiving fluid from a syringe, whereby the fluid expands the distal end when injected. In any or all embodiments, the catheter can comprise an output means to allow material from the abscess to drain out of the catheter.

BRIEF DESCRIPTION OF THE DRAWINGS

Embodiments are illustrated in the figures of the accompanying drawings, which are meant to be exemplary and not limiting, and in which like references are intended to refer to like or corresponding things.

FIG. 5 is a cross section of an embodiment of the medical device.

DETAILED DESCRIPTION OF THE PREFERRED EMBODIMENTS

Described are embodiments of a medical device comprising a balloon catheter having a distal end that is configured to inserted into an abscess wound and the balloon expanded. The balloon element includes an expandable antimicrobial or antibiotic material capable of absorbing fluid exudate from the abscess.

The device enables both a hydraulic and tapenade method of forcing or pressuring exudate into a drainage lumen within the catheter or absorbing it within material surrounding the distal tip of the catheter.

Figure 1:
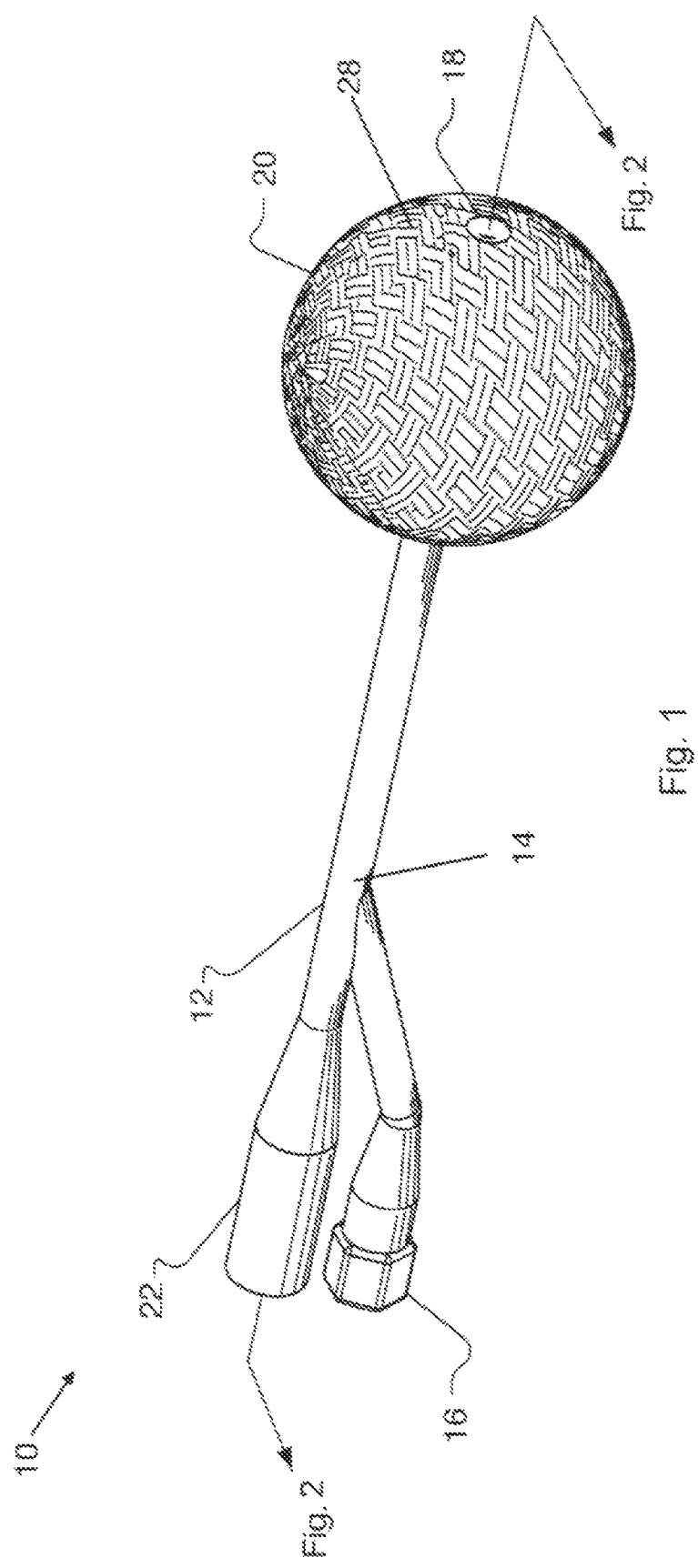
FIG. 1 is a perspective view of an embodiment of a medical device for treating abscesses.
Figure 2:
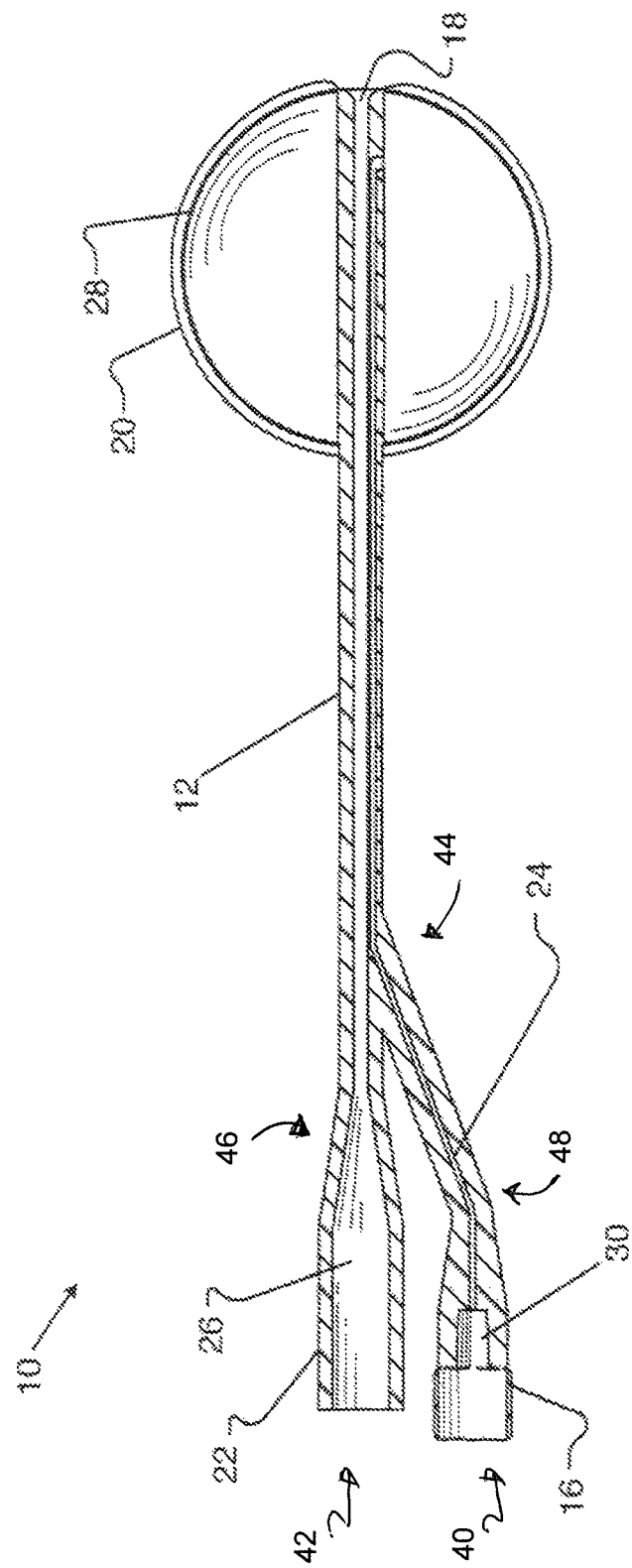
FIG. 2 is a side, cross section of the medical device of FIG. 1.

Referring now to the drawings, FIGS. 1-5 show embodiments of a medical device. Reference numerals have been assigned to generally refer as follows:
- 10: the device of the present invention
- 12: catheter
- 14: proximate end of catheter (12)
- 16: input port
- 18: distal end of the catheter (12)
- 20: flexible material
- 22: output port
- 24: balloon inflation passage
- 26: extravasation lumen
- 28: balloon interior
- 30: valve coupling
- 32: syringe
- 34: clogged pore
- 36: abscess cavity
- 38: skin surface FIG. 1 shows an embodiment of the medical device 10 configured to to treat or drain abscesses from human or animal tissue. The device 10 comprises a drainage catheter 12. The catheter can be partially, substantially entirely, or entirely flexible. The catheter can be constructed of an elastomeric biocompatible polymer, rubber or plastic material. In an embodiment, the material can be selected from silicone (siloxane) rubber, polyurethane, or other synthetic rubber, or latex rubber, or a compounded or composite combination of materials. The catheter 12 has a proximate end 14 with an input port 16 configured to engage with a syringe to inject fluid (e.g. liquid or air/gas) into the catheter 12. Opposite the proximate end 14 is a distal end 18 of the catheter 12. In an embodiment, the distal end 18 comprises an expandable balloon 28 that expands when fluid is injected via the input port 16. In an embodiment, the balloon 28 is at least partially or fully surrounded or encased by a flexible material 20 capable of sufficiently and resiliently stretching as the balloon 28 expands. The device may be fabricated by molding a material or composition of different materials by assembly, or via a coating such that the material properties of the catheter 12, port fitting and expandable region may be optimized for its intracavitary position. Other manufacturing techniques as known in the art can be used.

In an embodiment, the proximate end 14 of the catheter 12 further a bifurcation 44. A first arm 46 of the bifurcation 44 comprises an output port 22 configured to allow fluid to drain out of the catheter 12. The second arm 48 of the bifurcation 44 comprises the input port 16. In the embodiment shown in FIG. 2, the catheter 12 maintains two separate chambers 40, 42, referenced herein as a first chamber 40 and a second chamber 42, the first chamber 40 accessed by the input port 16, and the second chamber 42 accessed by the output port 22. The first chamber 40 accessed by the input port 16 comprises a balloon inflation passage 24 surrounded by a non-permeable membrane to prevent fluid exchange between the two chambers 40, 42. The balloon inflation passage 24 extends from the input port 16 to the interior of the balloon 28, which becomes inflated as fluid is injected into the input port 16. The second chamber 42 accessed by the output port 22 comprises an extravasation lumen 26 through which fluid may drain out of the catheter 12. The distal end 18 is permeable to allow fluid from the abscess to enter the extravasation lumen 26 and flow to the output port 22, from where the fluid may be drained. The input port 16 may further contain a seal or valve coupling 30 such that it allows for the passage of fluid from the inflation syringe 32 into the balloon inflation passage 24 and seals or closes the when the syringe 32 has been removed.

Figure 3:
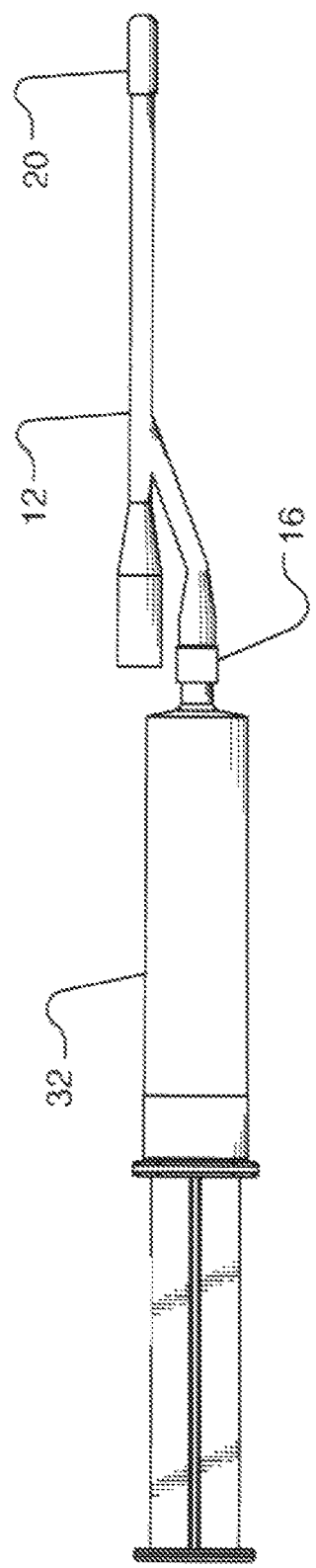
FIG. 3 is a side view illustrating the insertion of a syringe into the medical device of FIGS. 1 and 2.

FIG. 3 shows an embodiment of the device with an inflation syringe 32 interfacing with the input port 16. The device is shown in a deflated state.

Figure 4A:
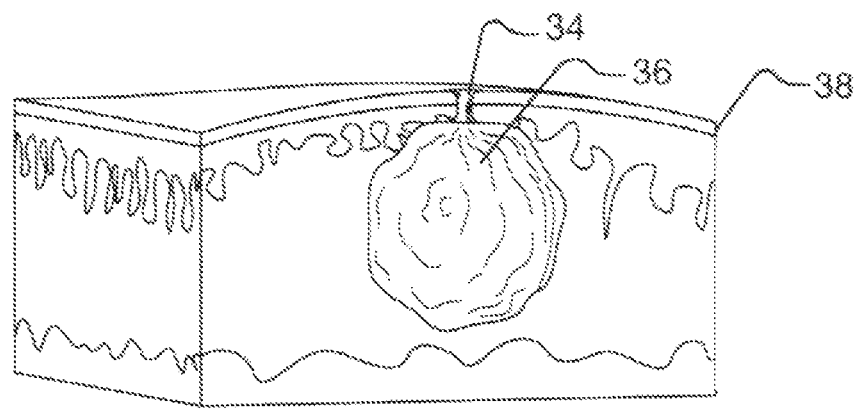
FIG. 4A is a cross sectional view of human tissue with an abscess.
Figure 4B:
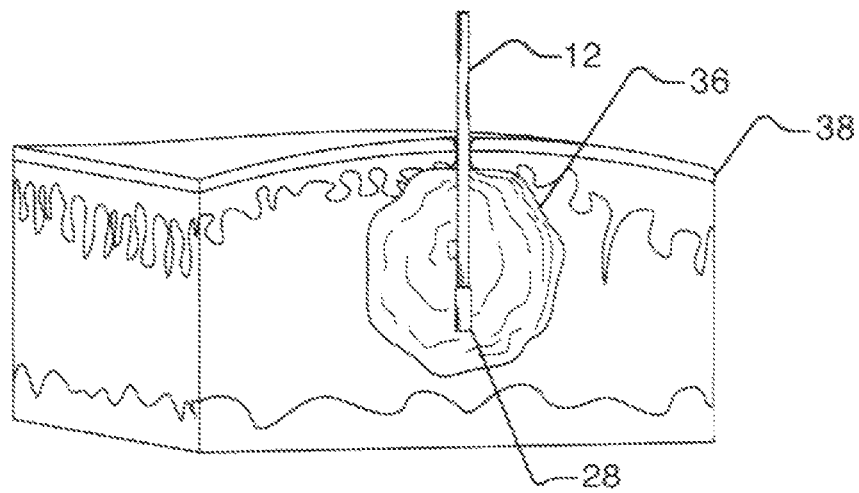
FIG. 4B is a cross sectional view of human tissue with an abscess with and embodiment of the medical device inserted in a deflated state.
Figure 4C:
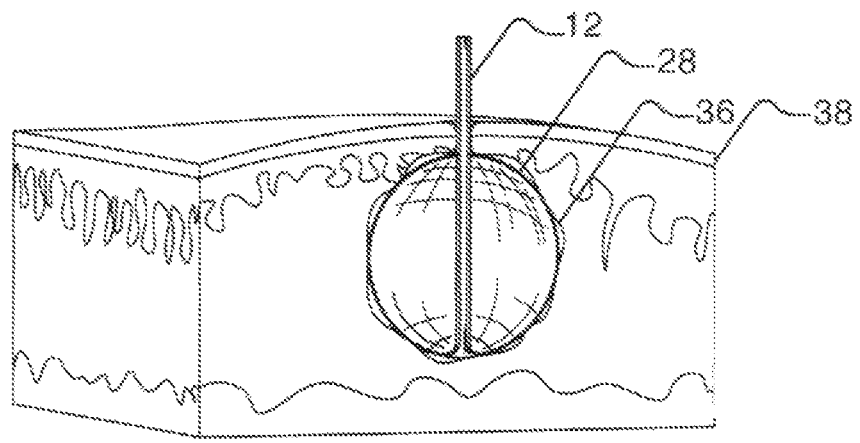
FIG. 4C is a cross sectional view of human tissue with an abscess with the medical device of the present invention inserted and then inflated.

FIGS. 4A-C show cross sections of human tissue with clogged pore 34 with underlying abscess. FIG. 4A shows pore 34 and abscess cavity 36 which lies below the skin's surface 38. The device 10 may be used by inserting the distal end 18 of catheter 12 into abscess cavity 36 with balloon 28 in a deflated state, as shown in FIG. 4B. Fluid is then injected via the input port 16. As fluid enters, the surface of balloon 28 stretches and expands, thus pushing the flexible material 20 toward and ultimately against the walls of the abscess cavity 36, filling the abscess cavity 36.

FIG. 4C shows the catheter 12 inserted into the abscess cavity 36, with balloon 28 inflated to fill the cavity 36. The flexible material 20 is absorbent, such that it may absorb fluid from the abscess. In an embodiment, the flexible material 20 can additionally include antimicrobial properties. For example, the flexible material 20 can comprise cotton, nylon or other synthetic polymer material, and may be treated or impregnated with an antimicrobial agent, a biologically fabricated hydrophilic material, or a compound or composite fabric. Antimicrobial agents such as, for example, silver, gold platinum, palladium, zinc, magnesium and copper can be embedded within the fibers of the fabric. This material may be of woven, non-woven, foam or other expandable elastic structure adhered to or coated upon the balloon 28 surface.

An exemplary clinical method of treating abscesses using the device is as follows:

1. The abscess is incised and drained in the standard manner with a scalpel. Pus is manually expressed and locutions are broken up with a hemostat. The cavity is then irrigated.
2. The distal end of the catheter is inserted into the wound cavity.
3. Using a syringe with fluid, the syringe is inserted into the input port and the contents of the syringe are injected into the catheter, causing the balloon to inflate. Injection of fluid continues until the balloon has reached sufficient expansion to tightly pack the cavity.
4. The catheter can be gently tugged so as to ensure proper inflation and expansion within the cavity.
5. The syringe is removed from the input port.
6. Gauze can be placed underneath the output port so as to absorb any drainage that may express during the next few days.
7. The patient can be given a syringe and instructions to deflate the balloon via the input port 16, or alternatively the catheter may be cut with scissors to cause deflation.
8. The device can be removed from the cavity and discarded.

FIG. 5 shows another embodiment of the device. The embodiment shown does not include a drainage port, but does comprise an input port 16 with valve coupling 30. Use of this embodiment is the same as previously described, except that there is no capability for fluid to drain from the abscess via the catheter 12.

Having thus described the invention with particular reference to embodiments described herein, various changes and modifications can be made therein without departing from the spirit and scope of the present invention as defined by the appended claims.

The invention claimed is:

1. A medical device comprising:
   a balloon catheter having a proximate end and an expandable distal end comprising an expandable balloon;
   the proximate end of the balloon catheter comprising an input port configured to receive fluid from a syringe that is configured to expand the balloon;
   said distal end of the balloon catheter comprising a region that is at least semi-permeable;
   said distal end further comprising a flexible absorbent material that is configured to absorb fluid exudate from an abscess into which the distal end is inserted
   wherein said distal end is expandable in toroidal directions;
   and an output port, wherein the output port is connected to a drainage lumen which is connected to the distal end that is configured to allow the absorbed fluid exudate in the distal end to drain through the output port.

2. The medical device of claim 1 wherein the catheter is at least partially flexible.

3. The device of claim 1 wherein the flexible absorbent material includes a flexible absorbent material selected from the group consisting of cotton, nylon, biologically fabricated material, synthetically fabricated material, or any polymer.

4. The device of claim 1 wherein the flexible absorbent material includes an antimicrobial agent.

5. The device of claim 4 wherein the flexible absorbent material includes an antimicrobial agent selected from the group consisting of silver, gold, platinum, palladium, zinc, magnesium, or copper.

6. The device of claim 1 wherein the input port comprises a one-way valve that is configured to engage with the syringe to allow fluid from the syringe be injected into said catheter and expand the distal end.

7. The device of claim 6 wherein the one way valve maintains the distal end expanded while the fluid exudate from the abscess drains out of said catheter.

8. The device of claim 7 wherein the drainage lumen is disposed inside the catheter disposed between the distal end and the output port.

9. The device of claim 1 wherein the expandable balloon is encased by a flexible material that is configured to stretch as the balloon expands.

10. The medical device according to claim 1 wherein the balloon catheter comprises a first chamber and a second chamber, the second chamber separated from the first chamber;
    the first chamber configured to be accessed by the input port, the first chamber comprising a balloon inflation passage surrounded by a non-permeable membrane that extends from the input port to the interior of the balloon; and
    the second chamber configured to be accessed by the output port and comprising an extravasation lumen connected to the at least semi-permeable distal end of the balloon catheter, the distal end configured to allow fluid from the abscess to enter the extravasation lumen and flow to the output port to drain out of the catheter.

11. The medical device according to claim 1, wherein the input port further comprises a valve coupling configured to allow for the passage of fluid into the balloon and seal the inflation passage to prevent fluid from exiting the input port.

12. The medical device according to claim 10, wherein the catheter comprises a bifurcation at the proximate end, a first branch of the bifurcation comprising the output port and a second branch of the bifurcation comprising the input port.

13. The medical device according to claim 12, wherein a portion of the balloon inflation passage of the first chamber from the bifurcation to the distal end and a portion of the extravasation lumen of the second chamber from the bifurcation to the distal end are disposed adjacent to one another with the catheter, and wherein the non-permeable membrane surrounding the balloon inflation passage is configured to prevent fluid exchange between the balloon inflation passage and the extravasation lumen.

14. A medical device comprising: a flexible catheter having a proximate end and an expandable distal end; the distal end comprising a region that is at least semi-permeable; the distal end including a flexible absorbent material that is configured to absorb fluid exudate from an abscess into which the distal end is inserted and expanded; the proximate end comprising an input port configured to engage with a syringe such that a fluid from the syringe can be injected into the catheter so as to expand said distal end wherein said distal end is expandable in toroidal directions; said proximate end further including an output port connected to a drainage lumen connected to the distal end and configured to allow the fluid exudate absorbed by the flexible absorbent material and within the distal end to drain out through the drainage lumen to the output port and out of the catheter, wherein the flexible catheter further comprises a first chamber and a second chamber, the second chamber separated from the first chamber;
   the first chamber configured to be accessed by the input port, the first chamber comprising a balloon inflation passage surrounded by a non-permeable membrane that extends from the input port to the interior of the expandable distal end; and
   the second chamber configured to be accessed by the output port and comprising an extravasation lumen connected to the at least semi-permeable distal end of the flexible catheter, the expandable distal end configured to allow fluid from the abscess to enter the extravasation lumen and flow to the output port to drain out of the catheter.

15. The medical device according to claim 14, wherein the catheter comprises a bifurcation at the proximate end, a first branch of the bifurcation comprising the output port and a second branch of the bifurcation comprising the input port, and a portion of the balloon inflation passage of the first chamber from the bifurcation to the distal end and a portion of the extravasation lumen of the second chamber from the bifurcation to the distal end are disposed adjacent to one another with the catheter, and wherein the non-permeable membrane surrounding the balloon inflation passage is configured to prevent fluid exchange between the balloon inflation passage and the extravasation lumen.

16. A method of treating a subcutaneous abscess comprising:
   treating the abscess with a medical device comprising: a flexible catheter having a proximate end and an expandable distal end, the distal end including a flexible, absorbent material that is configured to absorb fluid exudate from the abscess into which the distal end is inserted and expanded; the proximate end comprising an input port configured to engage a syringe such that the contents of the syringe can be injected into said catheter to expand the distal end, the proximate end further including an output port connected to a drainage lumen connected to the distal end and configured to allow the fluid exudate absorbed by the flexible absorbent material and within the distal end to drain out through the drainage lumen to the output port and out of the catheter, wherein the flexible catheter further comprises a first chamber and a second chamber, the second chamber separated from the first chamber;
   the first chamber configured to be accessed by the input port, the first chamber comprising a balloon inflation passage surrounded by a non-permeable membrane that extends from the input port to the interior of the expandable distal end; and
   the second chamber configured to be accessed by the output port and comprising an extravasation lumen connected to the at least semi-permeable distal end of the flexible catheter, the expandable distal end configured to allow fluid from the abscess to enter the extravasation lumen and flow to the output port to drain out of the catheter; wherein the treatment comprises:
   inserting the distal end into a subcutaneous wound abscess; and injecting the syringe's contents into the proximate end so as to expand the distal end, disconnecting the syringe and drain fluid from the output port.

17. The method of claim 16 wherein the syringe contents comprises saline or air.

18. The method of claim 16, further comprising: draining the abscess through an output port in said catheter.

19. The method according to claim 16, wherein the catheter comprises a bifurcation at the proximate end, a first branch of the bifurcation comprising the output port and a second branch of the bifurcation comprising the input port, and a portion of the balloon inflation passage of the first chamber from the bifurcation to the distal end and a portion of the extravasation lumen of the second chamber from the bifurcation to the distal end are disposed adjacent to one another with the catheter, and wherein the non-permeable membrane surrounding the balloon inflation passage is configured to prevent fluid exchange between the balloon inflation passage and the extravasation lumen.

* * * * *